United States Patent
Mullens et al.

[11] Patent Number: 6,119,465
[45] Date of Patent: Sep. 19, 2000

[54] SHIPPING CONTAINER FOR STORING MATERIALS AT CRYOGENIC TEMPERATURES

[76] Inventors: Patrick L. Mullens, 2124 Santiago St., Covina, Calif. 91724; Gregg Emmel, 1120 Princeton Dr., Marina Del Rey, Calif. 90292

[21] Appl. No.: 09/247,581

[22] Filed: Feb. 10, 1999

[51] Int. Cl.[7] .............................. B65B 63/08; F25D 3/08

[52] U.S. Cl. ................... 62/60; 62/371; 62/45.1

[58] Field of Search .............................. 62/60, 371, 45.1, 62/48.1, 48.3, 457.1

[56] References Cited

U.S. PATENT DOCUMENTS

| | | | |
|---|---|---|---|
| 4,729,494 | 3/1988 | Peillon et al. | 62/48.1 |
| 4,821,907 | 4/1989 | Castles et al. | 62/48.3 |
| 5,355,684 | 10/1994 | Guice | 62/54.2 |

Primary Examiner—William Doerrler

[57] ABSTRACT

A disposable shipping container for storing materials at cryogenic temperatures with: a specimen holding chamber, an open cell plastic foam material surrounding the specimen holding chamber for holding liquid nitrogen in suspension, a plurality of insulating and cushioning materials surrounding the plastic foam, a removable and replaceable primary cap for enclosing the specimen holding chamber allowing for the insertion and removal of the specimen from the specimen holding chamber and for adding liquid nitrogen to the plastic foam. A secondary removable and replaceable cap covers the primary cap. A preferred embodiment includes a specimen holding chamber that is comprised of a resin impregnated paper cylinder at its top half and a similarly sized stainless steel mesh screen cylinder attached to the lower edge of the paper cylinder at the specimen holders bottom half. The stainless steel cylinder has an attached stainless steel mesh floor at its lower most portion. The first and second rigid surrounding walls are joined at their top most portion and continue perpendicularly at their bottom most portions thereby forming a standard vacuum vessel. The plenum created by the first and second rigid walls contain an amount of either carbon dioxide or water vapor so that when liquid nitrogen is introduced to the plastic foam, the low temperature of the surrounding liquid nitrogen causes a vacuum to be created within the first and second rigid surrounding walls.

11 Claims, 4 Drawing Sheets

SHIPPING CONTAINER FOR STORING MATERIALS AT CRYOGENIC TEMPERATURES

FIELD OF INVENTION

This invention relates generally to the field of shipping containers and more particularly to a disposable shipping container for transporting biological materials at cryogenic temperatures.

BACKGROUND OF THE INVENTION

To ensure reproducible results in research and biotechnical processes, today's scientists and clinical practitioners have found it necessary to genetically stabilize living cells and preserve the integrity of complex molecules for storage and transport. This is accomplished by containing these materials in enclosures where cryogenic temperatures are continuously maintained at or near liquid nitrogen or vapor phase liquid nitrogen temperatures (77K and 100K respectively).

Advances in cryopreservation technology have led to methods that allow low-temperature maintenance of a variety of cell types and molecules. Techniques are available for the cryopreservation of cultures of viruses and bacteria, isolated tissue cells in tissue culture, small multicellular organisms, enzymes, human and animal DNA, pharmaceuticals including vaccines, diagnostic chemical substrates, and more complex organisms such as embryos, unfertilized oocytes, and spermatozoa. These biological products must be transported or shipped in a frozen state at cryogenic temperatures to maintain viability. This requires a shipping enclosure that can maintain a cryogenic environment for up to 10 days and meet other shipping requirements such as being relatively impervious to mechanical shock and effects of directional orientation.

In addition to the already existing difficulties posed in shipping heat-sensitive biologicals, the International Air Transport Association (IATA) imposed new regulations which became effective in January 1995 pertaining to all shipments that include specimens containing infectious agents or potentially infectious agents. These regulations, endorsed by the US Department of Transportation (DOT) and applicable to all public and private air, sea, and ground carriers, imposed greatly increased requirements upon shipping units to survive extensive physical damage (drop-testing, impalement tests, pressure containment tests, water damage) without leakage and without fracture of the internal containers (vials). Implementation of this regulation further complicated the shipping of frozen biologicals.

Even though bioshippers are currently available using LN2 as a refrigerant, little innovation has taken place in the design of packaging for low-temperature transport. Current shippers are generally vulnerable to the physical damage and changes in orientation encountered during routine shipping procedures. Additionally, these shippers do not comply with the IATA Dangerous Goods Regulation (effective January 1995, or as later amended). Commercial vendors have not developed or certified a cost-effective, standardized shipping unit with the necessary specimen capacity and hold time to meet user demands.

One of the main criticisms of current shippers is price, which varies from $500.00 to $1,000.00 per unit. This substantially limits their use for the transport of many biologicals. Because of the initial cost and limited production of these containers, they are designed to be reusable. However, the cost of return shipping of these heavy containers is significant, particularly in international markets.

Users also complain about the absorbent filler used in the current dry shippers, which breaks down with continuous use, contaminating the interior of the container. In fact, one large user of these containers has essentially centered their entire shipping operation around cleaning the broken down absorbent material from the inside of these containers after each use.

Another problem cited by users of currently available dry shippers relates to the functional hold time vs. static hold time. Static hold time pertains to a fully charged shipper with no heat load, sitting upright, e.g., essentially not in use. Functional hold time refers to the fully charged shipper in use and containing samples, e.g., in the process of being handled and transported. Even though the static hold time is promoted as being 20 days, if the container is tilted or positioned on its side, the hold time diminishes to hours as opposed to days. This occurs because the LN2 transitions to the gaseous (vapor) phase more rapidly resulting in outgassing. The LN2 can also simply leak out of the container when its positioned on its side.

The current cryogenic containers are promoted as being durable because they are of metal construction. However, rugged handling frequently results in the puncturing of the outer shell or cracking at the neck, resulting in loss of the high vacuum insulation. This renders them useless. The metal construction also adds to the weight of the container, thereby adding substantially to shipping costs.

Due to these deficiencies, and the realization that this current type of cryogenic shipper is not able to meet price and shipping rate goals, and that the biotechnical industry has become dependent on only one flawed system for solving cryogenic shipping demands, there is a need for a more reliable, less expensive, lightweight, semi-disposable cryogenic shipping container. By using unique, lightweight, low-cost, durable composites and polymers, the semi-disposable vapor phase LN2 bioshipper according to the present invention overcomes the above-mentioned disadvantages of the prior art. This is accomplished in an inherently simple, reliable, and inexpensive device which will result in reduced shipping costs, enhance reliability and safety, and fewer service requirements.

SUMMARY OF THE INVENTION

The primary objective of the invention is to provide a disposable cryogenic shipping container that is used one to five times and then discarded.

Another object of the invention is to provide a cryogenic shipping container that keeps its contents at or below 100K for up to ten days.

Another object of the invention is to provide a cryogenic shipping container that is inexpensive to manufacture.

A further object of the invention is to provide a cryogenic shipping container that conforms to the DOT/International Air Transport Association Dangerous Goods Regulations.

Yet another object of the invention is to provide a cryogenic shipping container that can be safely shipped in any orientation.

Still yet another object of the invention is to provide a cryogenic shipping container that can be "cryopumped" to produce a vacuum just prior to use.

Another object of the invention is to provide a cryogenic shipping container that is light in weight.

Another object of the invention is to provide a cryogenic shipping container that uses an inexpensive self-wetting material for retaining liquid nitrogen in-situ.

A further object of the invention is to provide a cryogenic shipping container that is not prone to breakage.

Another object of the invention is to utilize a vapor cooled shield to reduce heat transfer to the cryogen filled storage vessel.

Another object of the invention is to provide a cryogenic storage vessel (Dewar) made of a polymer or composite material.

Another object of the invention is to provide a surface coating for the polymer Dewar (vacuum container) to prevent leaking by gaseous diffusion.

Other objects and advantages of the present invention will become apparent from the following descriptions, taken in connection with the accompanying drawings, wherein by way of illustration and example, an embodiment of the present invention is disclosed.

SUMMARY

A disposable shipping container for storing materials at cryogenic temperatures comprising: a specimen holding chamber, a high surface area, low density, open cell plastic foam material surrounding said specimen holding chamber for retaining liquid nitrogen in-situ by absorption, adsorption, and surface tension; a plurality of insulating and cushioning materials surrounding said plastic foam, a removable and replaceable primary cap for both enclosing the said specimen holding chamber and for adding said liquid nitrogen to said plastic foam; a removable and replaceable secondary cap to further enclose the specimen holding container, and a third to fully enclose and encapsulate the entire shipping container system.

The drawings constitute a part of this specification and include exemplary embodiments of the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENT

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art how to employ the present invention in virtually any appropriately detailed system.

Figure 1:
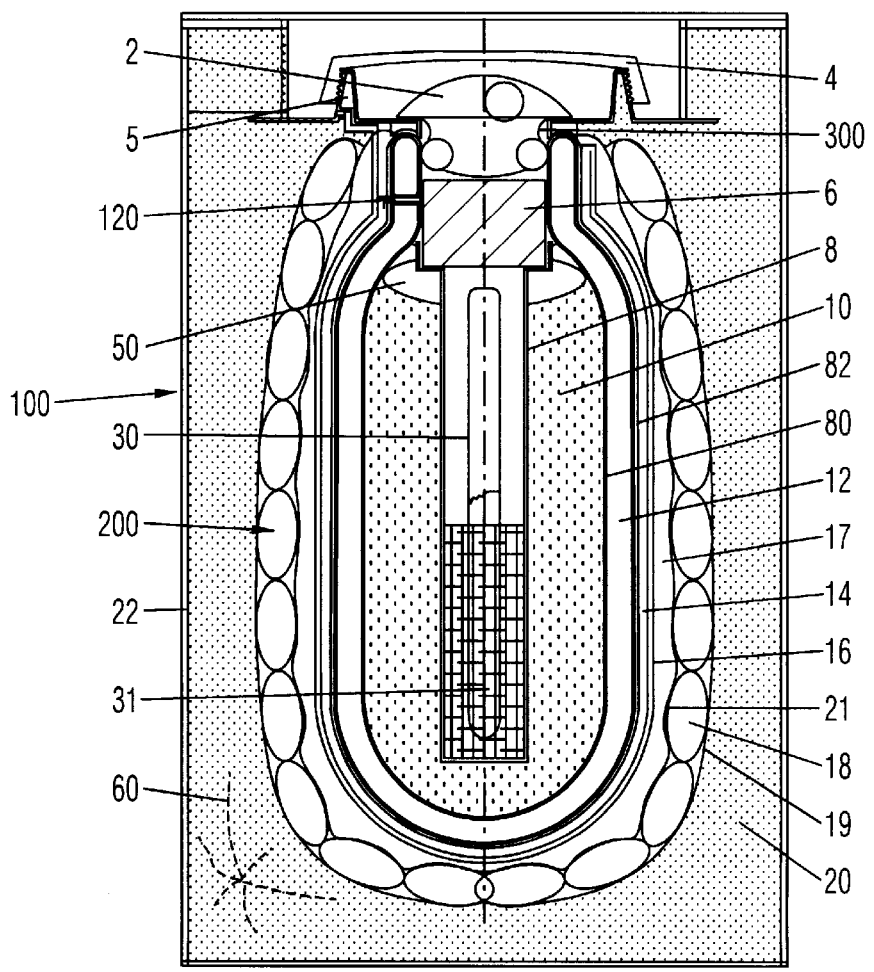
FIG. 1 is a side section view of the disposable cryogenic shipping container of the present invention.
Figure 3:
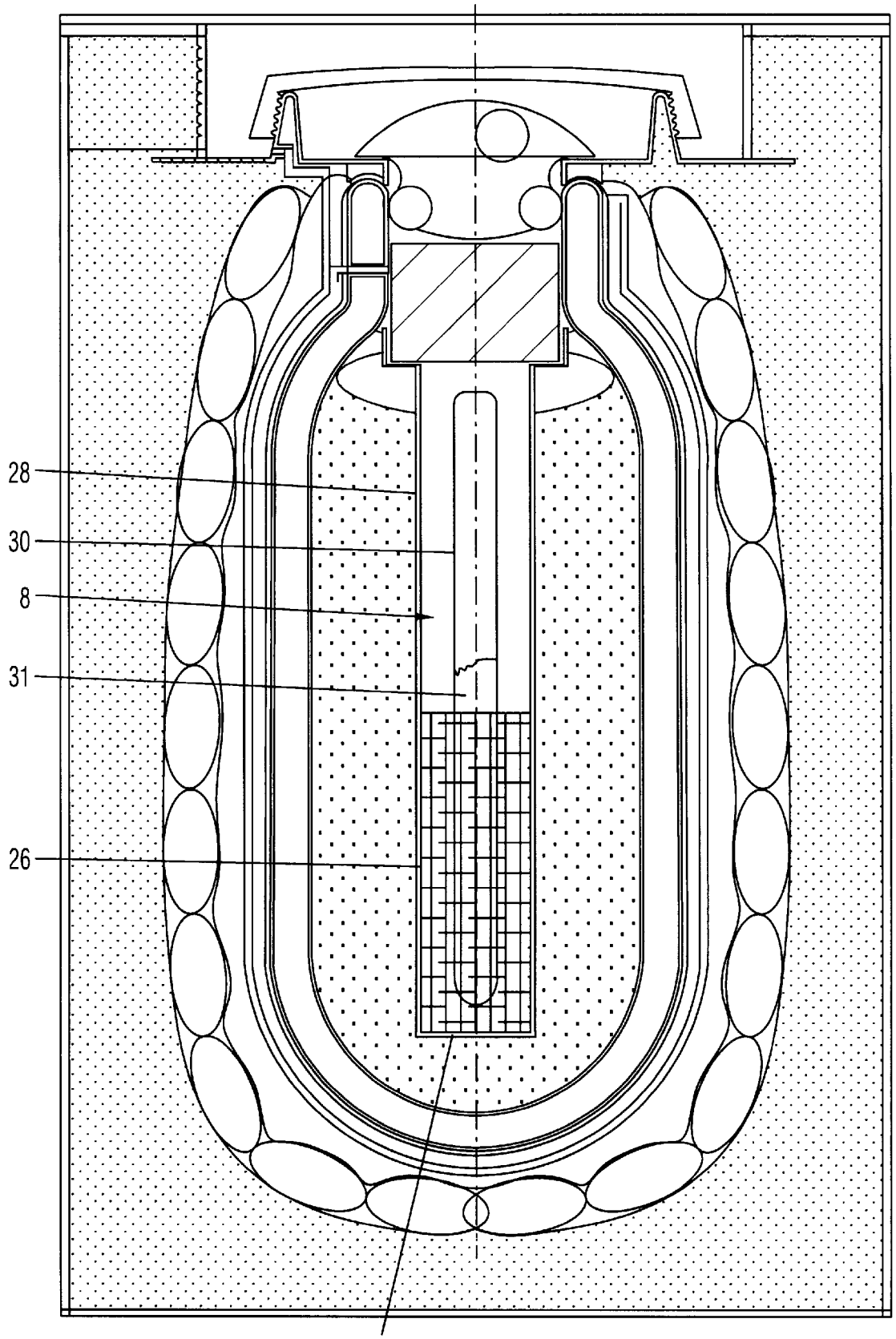
FIG. 3 is an enlarged side section view of the cryogenic shipping container of the present invention.

Referring now to FIG. 1. A side section view of the disposable cryogenic shipping container 100 of the present invention is seen. A specimen such as sperm or serum is contained in a straw-shaped carrier or 2 ml vial 30 and inserted into the specimen chamber 8 of the present invention. Specimen chamber 8 is further defined in FIG. 3 where one sees that the chamber 8 is comprised of a cylindrical top half 28 which is made of resin impregnated paper and an attached lower half 26 made of stainless steel mesh screen. Screen 26 terminates at its bottom end in a mesh floor 24 made of the same material as the screen side walls.

Referring back to FIG. 1, one sees that the specimen chamber 8 is surrounded by an open cell plastic foam such as phenolic foam 10 which is inexpensive and commonly used as a water-holding base for floral arrangements. The foam can either be foamed in place or it can be premanufactured in blocks and then broken down into chunks and inserted into the space surrounding the specimen chamber 8. Plastic foam 10 such as phenolic foam is an important contribution to the present invention 100 in that previous cryogenic shipping containers use denser more expensive, and brittle substrates such as a porous magnesium-based material or a fibrous ceramic material that can chip and break down into a powder during shipping thereby contaminating the interior of the specimen chamber. Liquid cryogen such as LN2 60 is poured into the plastic foam, and the open cell structure of the foam 10 retains the liquid nitrogen 60 by absorption, adsorption, and surface tension as it saturates the foam 10. It is important to note that the plastic foam filler material of the present invention absorbs cryogen such as LN2 up to six times faster than previously used materials. This feature accelerates the process of charging the cryogenic refrigerator with cryogen. The physical properties of a cryogen such as liquid nitrogen 60 and the plastic foam 10 are such that the cryogen remains in the plastic foam 10 and does not migrate into the specimen chamber 8 even though the bottom half of the specimen chamber 8 is constructed of porous screen material 26. The plastic foam 10 has a free volume of greater than 95% which is considerably better on a weight and cost basis than currently utilized materials. The plastic foam 10 is an azotephilic absorbent capable of acquiring and retaining in place the LN2 cryogen because of the high surface tension which exists between the LN2 and the foam. As a result, the shipping container 100 of the present invention can be shipped in any orientation, including upside down, without danger of spilling or having the liquid nitrogen directly contact the specimen vial. A doughnut shaped partition 50 constructed of a rigid sponge material acts to retain the plastic foam 10 in place. A removable and replaceable polyurethane foam spacer 6 sits atop the specimen chamber 8 to hold specimen 30 in place and to act as a top insulator.

As a first line of insulation, the cryogen-saturated foam 10 is contained within a vacuum bottle (Dewar) as shown in FIG. 1 consisting of a first wall 80 and a second wall 82. Walls 80, 82 progress downward and form a curved bottom as in the case with standard vacuum bottles. The vacuum bottle is currently made of glass because glass does not transmit gas through its walls thereby enhancing its ability to retain a vacuum. The vacuum bottle of the present invention 100 can be made of glass; however, recent advances in plastics technology make it possible to fabricate the vacuum bottle 80, 82 out of a plastic or composite which possesses gas barrier qualities and suitable low temperature properties using common manufacturing techniques such as blow molding or injection molding. Certain polyamides such as Durethan@ polyamide 6 can be used for this purpose. Other techniques such as applying a surface coating of triple distilled vacuum oil such as parylene to the exterior walls of the plastic vacuum bottle can be used to close the microscopic pores of the plastic and further reduce the probability of gas diffusion in or out of the vacuum space. Obviously, a plastic vacuum bottle is advantageous as the chance of breakage is greatly reduced during shipping.

Another important feature of the vacuum bottle 80, 82 is that a fill gas, such as carbon dioxide or water vapor, can be suffused into the space defined by walls 80, 82. The fill gas is chosen to have the property that upon cooling to LN2 temperatures (77K) it will condense into a solid having the vapor pressure of a high vacuum ($10^{-7}$ to $10^{-13}$ Torr). When liquid nitrogen 60 is absorbed into plastic foam 10, the low temperature of the liquid nitrogen at 77K acts on the fill gas to create a vacuum by cryopumping in the space between walls 80 and 82. In this way the user creates a very high vacuum by cryopumping only when the shipping container 100 is about to be used. This means that a very high vacuum is produced by cryopumping only at the time such a vacuum is needed; a vacuum so produced is not subject to degradation as it is renewed each time it is needed; a better quality vacuum is achieved by cryopumping than can be produced by conventional techniques now employed; and when not cold, the vacuum space actually contains the fill gas at a positive pressure, acting to prevent the infusion of atmospheric gases.

Figure 4:
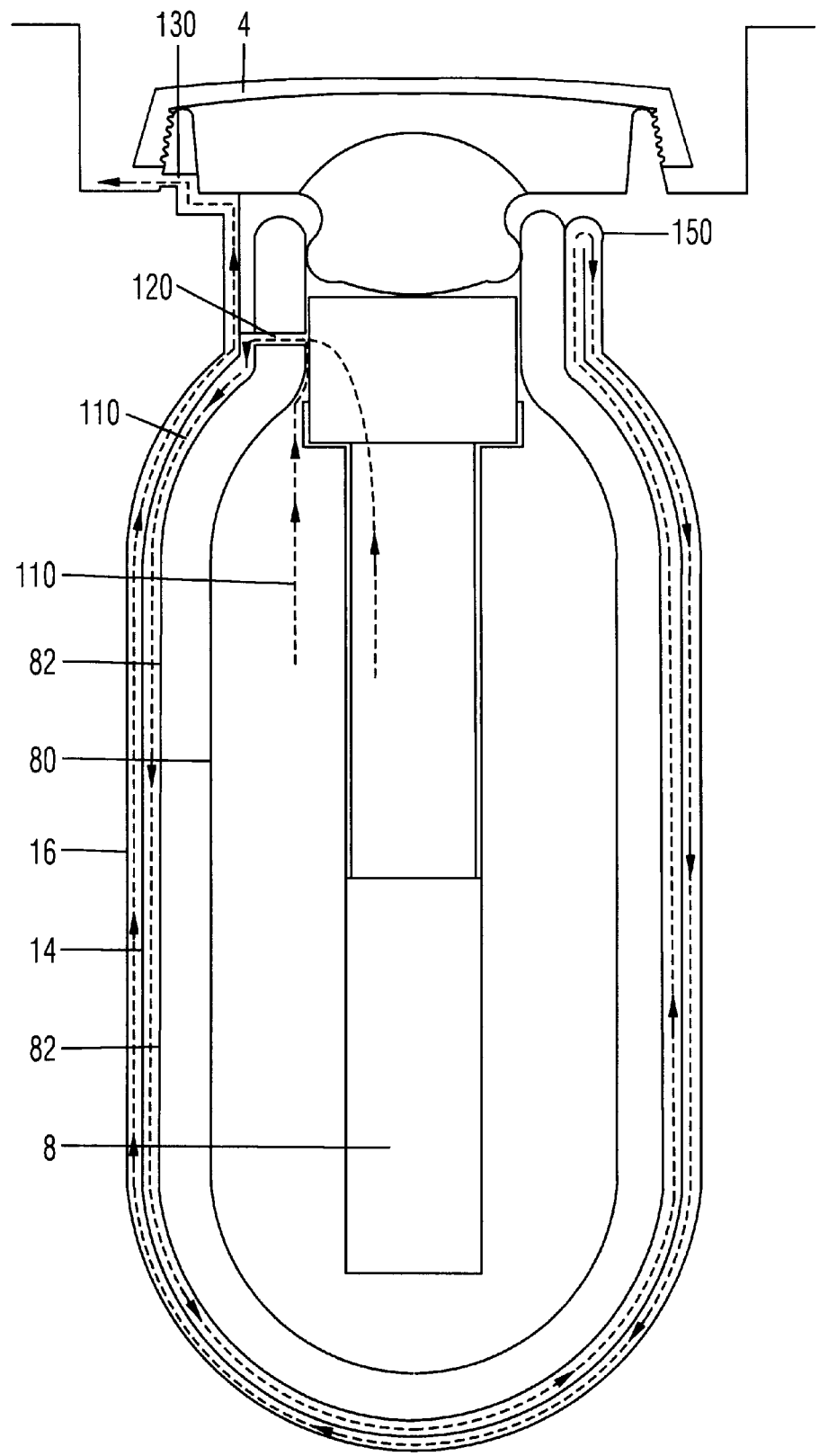
FIG. 4 is a schematic side section view showing the vapor cooled shield and venting system of the present invention.

An effective method of reducing heat transfer to the storage vessel is incorporated into the venting system of the present invention. This entails using the cold vent gas produced by heat transfer to the cryogen in the vacuum bottle to create an intermediate shield or vapor cooled shield to intercept some of the heat which would otherwise find its way to the cryogen in the vacuum storage vessel. Referring again to FIG. 1, we see a plurality of walls 14, 16 surrounding vacuum bottle 80, 82. These walls 14, 16 and the channels created by them can be seen clearly in FIG. 4. All heat transfer by radiation and conduction must pass though spaces 14, 16 before reaching the stored cryogen. Accordingly, the vent gas (vapor) 110 travels in an upward direction and passes through a channel 120 in vacuum bottle 80, 82. The vapor 110 is guided by wall 14 and progresses down the space created between wall 82 and wall 14. The vapor 110 reaches the top portion 150 and travels back down between wall 14 and wall 16, finally exiting through a small channel 130 located just below the secondary cap 4. In this way walls 14 and 16 create a convoluted channel for routing the vent gasses 110 to the open atmosphere. At the same time, the vent gas in the channel is utilized to intercept heat and act as a vapor cooled shield. No expensive materials or fabrication techniques are required. A similar effect can be produced by routing the vent gases through coiled tubing located in the vacuum space between walls 80, 82 prior to exiting to the atmosphere.

Referring again to FIG. 1, we see further layers of insulation and cushioning which will now be explained. Beyond wall 16 is a layer of polyurethane foam 17 which helps protect and insulate the vacuum bottle 80, 82. The next layer of encasement is a gas filled bladder assembly 200 comprised of a plurality of pockets formed by intermittent welding of flexible polymer wall 19 to flexible polymer wall 21. Gas 18 is pumped into bladder assembly 200 and the assembly is then sealed, thereby trapping the enclosed gas 18. The bladder assembly 200 further insulates the vacuum bottle 80, 82, but more importantly acts as a shock absorber for vacuum bottle 80, 82, thereby protecting it from mechanical shock during shipping and handling. The next insulating and cushioning barrier is formed by polyurethane foam 20 which fills the space created between flexible polymer bladder 19 and outer protective corrugated plastic housing 22.

Figure 2:
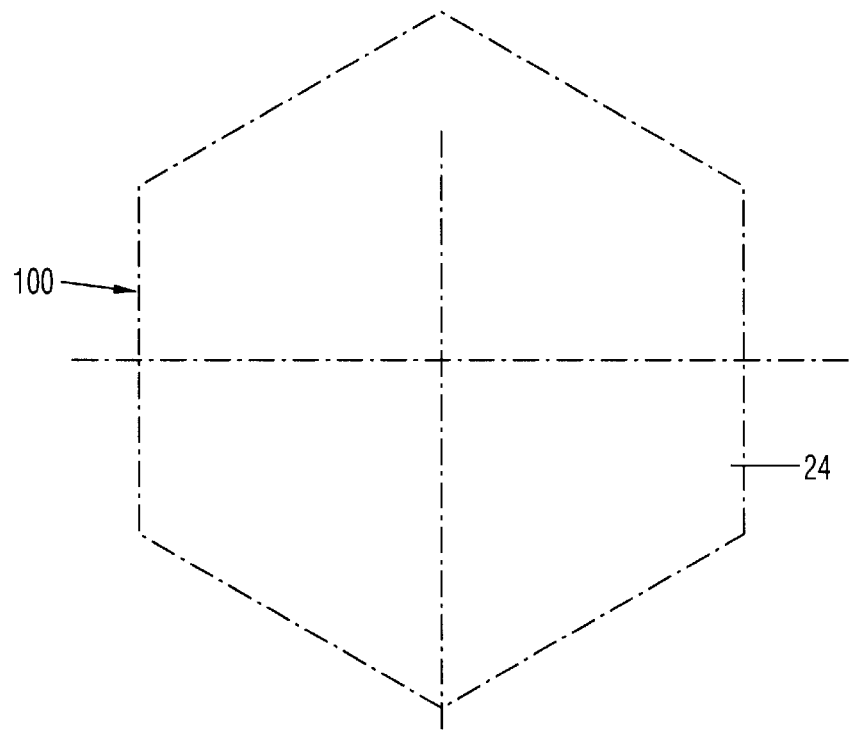
FIG. 2 is a top view of the disposable cryogenic shipping container of the present invention.

FIG. 2 shows a top view of the shipping container 100 of the present invention. The hexagonal shape 24 shown is a preferred embodiment; however, the outer contour could be any number of shapes, including round, square or rectangular. It is also obvious that any number of vacuum bottles 80, 82 and associated insulating and cushioning barriers could be assembled within one outer housing 22.

Figure 5:
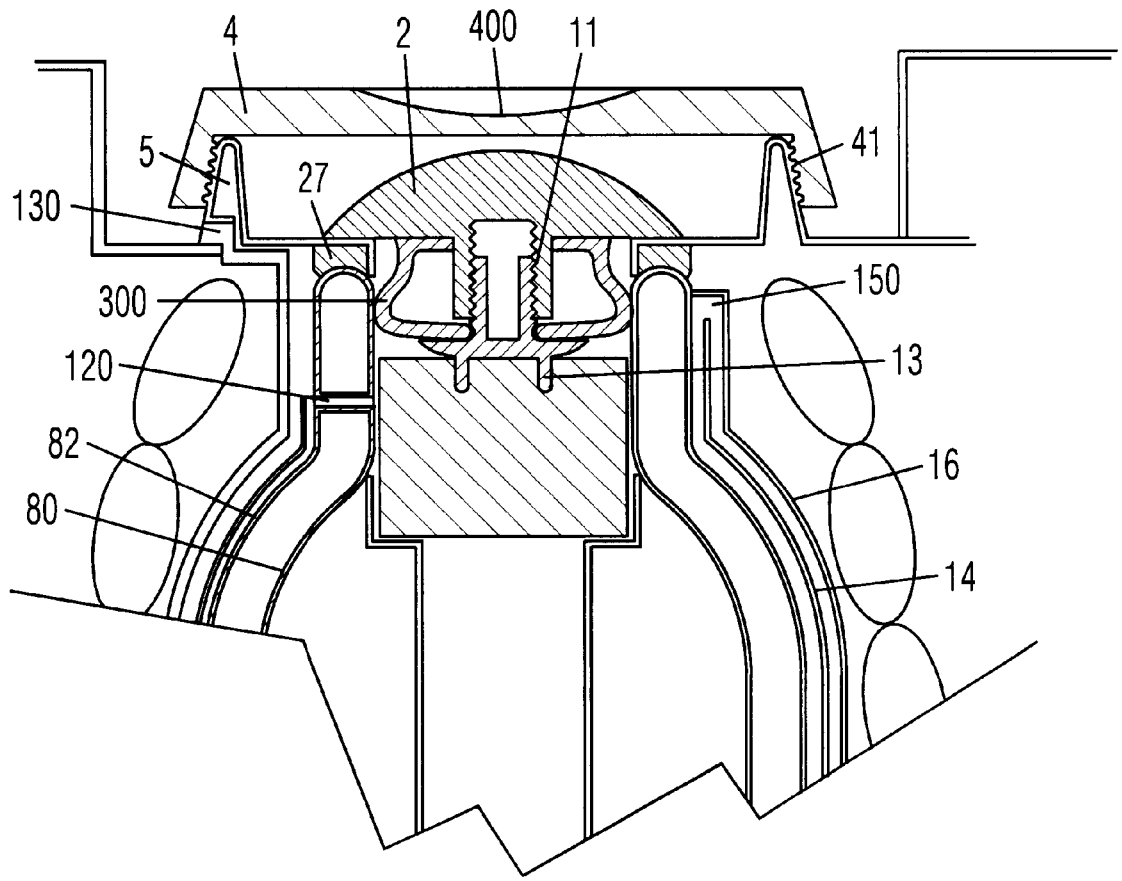
FIG. 5 is a detailed side section view of the primary and secondary closure mechanisms of the present invention.

FIG. 5 shows an enlarged section view of the top cap portion of the present invention 100. Secondary cap 4 screws 41 onto top collar 5. Primary cap 2 is inserted into the mouth of vacuum bottle 80, 82. Top cap 2 screws 11 down on cap retainer 13 and in so doing, causes resilient rubber shirt gasket 300 to expand firmly against the vacuum bottle wall 80. Silicone gasket 27 acts as a sealing member between the vacuum bottle 80, 81 and top collar 5. Protrusions 13 fit into matching indentations in foam plug 6, thereby preventing cap retainer 13 from spinning during the tightening process. Indentation 400 can act as a cap-supporting device when cap 2 is removed.

In this way, the shipping container 200 of the present invention solves the important problems associated with shipping biologicals at cryogenic temperatures. The container is relatively light in weight compared to the heavy steel containers currently being used. Although there are a number of insulating and cushioning materials used in the present invention 100, they are commonly available materials that are easy to form and manufacture, thereby making the shipper of the present invention 100 quite inexpensive as compared to current cryogenic shippers. The shipper of the present invention complies with the IATA Dangerous Goods Regulations which is not the case with most current cryogenic shippers. The shipper of the present invention 100 can be charged with cryogen such as liquid nitrogen quickly and when completely charged, can maintain cryogenic temperatures for up to ten days.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A disposable shipping container for storing materials at cryogenic temperatures comprising a specimen holding chamber, an open cell plastic foam material surrounding said specimen holding chamber for holding liquid nitrogen in suspension, a plurality of insulating and cushioning materials surrounding said plastic foam, a removable and replaceable primary cap for enclosing the said specimen holding chamber allowing for the insertion and removal of the specimen from said specimen holding chamber and for adding said liquid nitrogen to said plastic foam and a secondary removable and replaceable cap for covering said primary cap.

2. A disposable shipping container for storing materials at cryogenic temperatures as claimed in claim 1 wherein said specimen holding chamber is comprised of a resin impregnated paper cylinder at its top half and a similarly sized stainless steel mesh screen colander attached to the lower edge of said paper cylinder at said specimen holders bottom half, said stainless steel colander having an attached stainless steel mesh floor at its lower most portion.

3. A disposable shipping container for storing materials at cryogenic temperature as claimed in claim 1 wherein said absorbent material is plastic foam that has a porosity of 95% or more.

4. A disposable shipping container for storing materials at cryogenic temperatures as claimed in claim 1 wherein said plurality of insulating and cushioning materials include sequentially a first rigid surrounding wall, an evacuated surrounding air space, second rigid surrounding wall, a first ambient air space surround, a third rigid surrounding wall, a second ambient air space surround, a fourth rigid surrounding wall, a fifth surrounding layer of polyurethane foam, a sixth surrounding layer consisting of a flexible gas inflated polymer bladder, a seventh surrounding layer of polyurethane foam and a final surrounding protective covering made of corrugated plastic.

5. A disposable shipping container for storing materials at cryogenic temperatures as claimed in claim 2 wherein said first and second rigid surrounding walls are joined at their top most portion and continue perpendicularly at their bottom most portions thereby forming a double walled vessel, the plenum created by said first and second rigid walls containing an amount of either carbon dioxide or water vapor so that when said liquid nitrogen is introduced into said plastic foam, the low-temperature of said surrounding liquid nitrogen causes a vacuum to be created within said first and second rigid surrounding walls.

6. A disposable shipping container for storing materials at cryogenic temperatures as claimed in claim 1 wherein said first rigid surrounding wall forms a vessel opening that is cylindrical in shape and is capable of being covered by an insertable said primary cap, said insertable portion of said primary cap having a compressible resilient gasket forming an air tight seal between said cap and said first rigid wall.

7. A disposable shipping container for storing materials at cryogenic temperatures as claimed in claim 1 wherein said opening of said specimen holding chamber is capped by an insertable and removable closed cell urethane foam portion.

8. A disposable shipping container for storing materials at cryogenic temperatures as claimed in claim 1 wherein said plastic foam is capped by a doughnut shaped portion of open cell sponge material, said specimen holding chamber capable of protruding through said sponge material.

9. A disposable shipping container for storing materials at cryogenic temperatures as claimed in claim 2 wherein said third rigid surrounding wall terminates at its top most point in a lip and wherein said fourth said rigid surrounding wall terminates at its top most point in an inwardly facing perpendicularly disposed flange, said flange terminating at its inner most point at the outer wall of said second rigid wall thereby creating an undulating path for escaping liquid nitrogen vapor, said nitrogen vapor starting its escape from a small opening, said opening being perpendicularly disposed to and piercing the walls of said second and third rigid walls at the top neck section of said second and third rigid walls, said vapor continuing its path between said second and third walls and at the bottom of said third wall continues to the space between said third wall and said fourth wall, said vapor traveling upwardly and finally escaping to the atmosphere through a small opening just below said secondary cap.

10. A disposable shipping container for storing materials at cryogenic temperatures as claimed in claim 4 wherein said first rigid surrounding wall and said second rigid surrounding wall are constructed of a rigid plastic material.

11. A disposable shipping container for storing materials at cryogenic temperatures as claimed in claim 10 wherein the outer surface of said second rigid surrounding wall is coated with a micro porous sealant such as triple distilled vacuum oil.

\* \* \* \* \*